United States Patent
Berger et al.

(10) Patent No.: US 6,454,410 B1
(45) Date of Patent: Sep. 24, 2002

(54) MOSAICING AND ENHANCEMENT OF IMAGES FOR OPHTHALMIC DIAGNOSIS AND DOCUMENTATION

(75) Inventors: Jeffrey W. Berger, Cherry Hill; Jane Asmuth, Princeton; Steve Hsu, Cranbury, all of NJ (US); Paul Sajda, New York, NY (US)

(73) Assignees: The Trustees of the University of Pennsylvania, Philadelphia, PA (US); Sarnoff Corporation, Princeton, NJ (US)

(*) Notice: Subject to any disclaimer, the term of this patent is extended or adjusted under 35 U.S.C. 154(b) by 0 days.

(21) Appl. No.: 09/692,939

(22) Filed: Oct. 20, 2000

Related U.S. Application Data

(60) Provisional application No. 60/160,538, filed on Oct. 20, 1999, and provisional application No. 60/224,995, filed on Aug. 14, 2000.

(51) Int. Cl.[7] .............................................. A61B 3/14
(52) U.S. Cl. ....................................................... 351/206
(58) Field of Search ................................ 351/206, 209, 351/210, 211, 246; 382/117

(56) References Cited

U.S. PATENT DOCUMENTS

| | | | |
|---|---|---|---|
| 5,159,647 A | 10/1992 | Burt | 382/37 |
| 5,325,449 A | 6/1994 | Burt et al. | 382/56 |
| 5,488,674 A | 1/1996 | Burt et al. | 382/284 |
| 5,629,988 A | 5/1997 | Burt et al. | 382/276 |
| 5,649,032 A | 7/1997 | Burt et al. | 382/284 |
| 5,684,561 A | 11/1997 | Yancey | 351/209 |
| 5,912,720 A | 6/1999 | Berger et al. | 351/206 |
| 6,215,891 B1 * | 4/2001 | Suzaki et al. | 351/206 |

OTHER PUBLICATIONS

U.S. application No. 60/160,538, filed Oct. 20, 1999, pending.
U.S. application No. 60/224,995, filed Aug. 14, 2000, pending.
Sawhney, et al., "Robust Video Mosaicing through Topology Inference and Local to Global Alignment", *Computer Vision–ECCV'98*, Freiburg, Germany, Jun. 1998, vol. 2, 103–119.

\* cited by examiner

*Primary Examiner*—George Manuel
(74) *Attorney, Agent, or Firm*—Woodcock Washburn LLP

(57) ABSTRACT

The invention is a method and system for mosaicing images of the eye to create high resolution, wide-field ophthalmic images for the diagnosis and treatment of eye diseases. The inventive method acquires a first image of the eye, acquires a second image of the eye, and processes the images to produce a mosaic representation. The second image includes a portion of the first image. To guide in acquiring the second image, the method may view the first image while acquiring the second image. The images typically are acquired using either a direct ophthalmoscope or a slitlamp biomicroscope. The method further may convert the images to a digital format. The step of processing includes aligning and merging the images, and conducting real-time processing and non-real-time processing. Real-time processing may include eliminating non-overlapping images, image registration, topology inference, local-to-global alignment, image fusion, signal estimation, and multiresolution blending, while the non-real-time processing may include local alignment, global alignment, image registration, intra-alignment, inter-alignment, signal averaging, and photometric blending.

36 Claims, 4 Drawing Sheets

MOSAICING AND ENHANCEMENT OF IMAGES FOR OPHTHALMIC DIAGNOSIS AND DOCUMENTATION

CROSS-REFERENCE TO RELATED APPLICATIONS

This application claims priority under 35 U.S.C. §119(e) to U.S. Provisional Patent Applications Serial No. 60/160,538, which was filed on Oct. 20, 1999, and Serial No. 60/224,995, which was filed on Aug. 14, 2000, and these applications are hereby incorporated by reference in their entireties.

FIELD OF THE INVENTION

The present invention relates to the field of mosaicing images. More specifically, the present invention relates to mosaicing, images of the eye to create high resolution, wide-field ophthalmic images for the diagnosis and treatment of eye diseases.

BACKGROUND OF THE INVENTION

Diagnosis and treatment of ophthalmic disease in general, and retinal and optic nerve diseases in particular, rely heavily on photographic and angiographic imaging of the eye. These images are vital for clinical care in preventing and treating the most common causes of vision loss, including diabetic retinopathy and age-related macular degeneration. Photographic and angiographic images facilitate discovery of ophthalmic abnormalities by documenting changes to the eye over time. For example, abnormalities may be discovered in real-time by comparing images taken during a patient examination with previously taken photographic images.

To date, photographic images of the fundus (back of the eye or retina) are acquired with a standard fundus camera, available commercially from Carl Zeiss, Inc., model number FF450. The fundus camera provides a high quality, wide-field of view image of the fundus. However, because of its high cost and the fact that it is a dedicated instrument, offering no use other than photography, many optometrists and ophthalmologists opt not to have a fundus camera in their office. Therefore, fundus photography, is rarely performed during the routine examination that a majority of patients undergo. As a result, fundus photography is underutilized.

A direct ophthalmoscope and slitlamp biomicroscope, on the other hand, are instruments that are common to every examination room in an ophthalmologist's and optometrist's office. Furthermore, these instruments may be are attached to an image acquisition device, like a charge coupled device (CCD) camera. The CCD camera in combination with the direct opthalmoscope and slitlamp can acquire images of the back of the eye for documentation and communication purposes. However, because the direct ophthalmoscope and biomicroscope provide a reduced image quality and a far narrower field of view (as compared to the fundus camera), the images they provide are not useful for photodocumentation.

Presently, image processing techniques exist that construct mosaic representations from individual still and video imagery. These techniques include image registration, topology inference with local-to-global alignment (TILGA), and multiresolution blending, well known to those skilled in the art. Generally, partially overlapping individual images are combined and manipulated (using these processes) to provide a seamless mosaic effect. In particular, image registration refers to the alignment of the individual images. Topology inference is a process that automatically determines which image pairs are indeed overlapping, and local-to-global alignment simultaneously adjusts the placement of each image to be maximally consistent with all the pair-wise alignments. Multiresolution blending smoothly transitions the color and brightness between adjacent images, which otherwise may be radiometrically mismatched due to non-uniform illumination and sensor sensitivity. The mosaic's overall resolution can be improved by signal estimation from overlapping images. In addition, image fusion may be used to enhance focus and dynamic range of the mosaic by combining the most salient features of each image at multiple resolutions.

Although these processing techniques have been successful in producing wide field of view mosaics in various applications (e.g., indoor, outdoor, and microscopic applications), they have failed when applied to direct ophthalmoscope and slitlamp imagery. This failure is due, in part, to the many unique characteristics of such imagery such as: narrow field of view, rapid movement of the subject eye, specular reflections, areas of low feature contrast, and geometric image distortion. Therefore, it would be useful to provide a system and method for mosaicing direct ophthalmoscope and slitlamp images.

SUMMARY OF THE INVENTION

In view of the above-mentioned limitations in the prior art, the present invention describes techniques for converting the direct ophthalmoscope's and slitlamp biomicroscope's low-quality, narrow field of view images into clinically useful high-quality, wide field of view images.

The invention is a method and system for mosaicing images of the eye to create high resolution, wide-field ophthalmic images for the diagnosis and treatment of eye diseases. The inventive method comprises acquiring a first image of the eye, acquiring a second image of the eye, and processing the images to produce a mosaic representation. The second image includes a portion of the first image. To guide in acquiring the second image, the method may include the step of viewing the first image while acquiring the second image. The method also may include the step of providing a direct ophthalmoscope or a slitlamp biomicroscope to acquire the images. The method further may comprise converting the images to a digital format. The step of processing includes aligning and merging the images, and conducting real-time processing and non-real-time processing. Real-time processing may include eliminating non-overlapping images, image registration, topology inference, local-to-global alignment, image fusion, signal estimation, and multiresolution blending. Non-real-time processing may include local alignment, global alignment, image registration, intra-alignment, inter-alignment, signal averaging, and photometric blending.

The inventive system for mosaicing images of the eye comprises an image acquisition device adapted to provide images of the eye, a camera coupled to the image acquisition device, a data processor coupled to the camera, a data storage device couple to the data processor, and a monitor coupled to the data processor. The image acquisition device may be a direct opthalmoscope or a slitlamp biomicroscope. The system also may include a selection unit coupled to the data processor, wherein the selection unit may be a keyboard, a mouse, or a microphone. The system further may include a converter coupled to the image acquisition device and the data storage device. The data processor may conduct both real-time and non-real-time processing. The real-time processing may include eliminating non-overlapping images, image registration, topology inference, local-to-global alignment, image fusion, signal estimation, and multiresolution blending. The non-real-time processing may include image registration, topology inference, local-to-global alignment, image fusion, signal estimation, and/or multiresolution blending.

The invention further includes a method of detecting eye diseases. The inventive method comprises examining the eye using an image acquisition device, capturing images of the eye, wherein each of the images includes a portion of another image, aligning and merging the images to create a mosaic representation, viewing the mosaic representations, and detecting eye diseases. The step of examining may be conducted using a direct ophthalmoscope or a slitlamp biomicroscope.

The invention also includes a method of creating a mosaic representation of the eye. The method comprises providing an image acquisition device adapted to acquire images of the eye. The image acquisition device may include, for example, a direct ophthalmoscope or a slitlamp biomicroscope. The image acquisition device allows a user to select a first image of a first portion of the eye. The user then moves the image acquisition device to a second portion of the eye, wherein the second portion overlaps the first portion. A second image of the second portion of the eye is then acquired. As the image acquisition device is moved, the first image may be viewed to assist in ensuring overlap with the second image. Acquiring the second image may include automatically capturing images from a stream of images provide by the image acquisition device. The images are processed to create a mosaic representation of the eye. The processing may include merging and aligning the images.

BRIEF DESCRIPTION OF THE DRAWINGS

The foregoing and other novel features and advantages of the invention will become more apparent and more readily appreciated by those skilled in the art after consideration of the following description in conjunction with the associated drawings, of which.

DETAILED DESCRIPTION OF THE PRESENTLY PREFERRED EMBODIMENTS

A preferred embodiment of the invention will now be described in detail with reference to FIGS. 1–4. Those skilled in the art will appreciate that the description given herein with respect to those figures is for exemplary purposes only and is not intended in any way to limit the scope of the invention. All questions regarding the scope of the invention may be resolved by referring to any appended claims.

Figure 1:
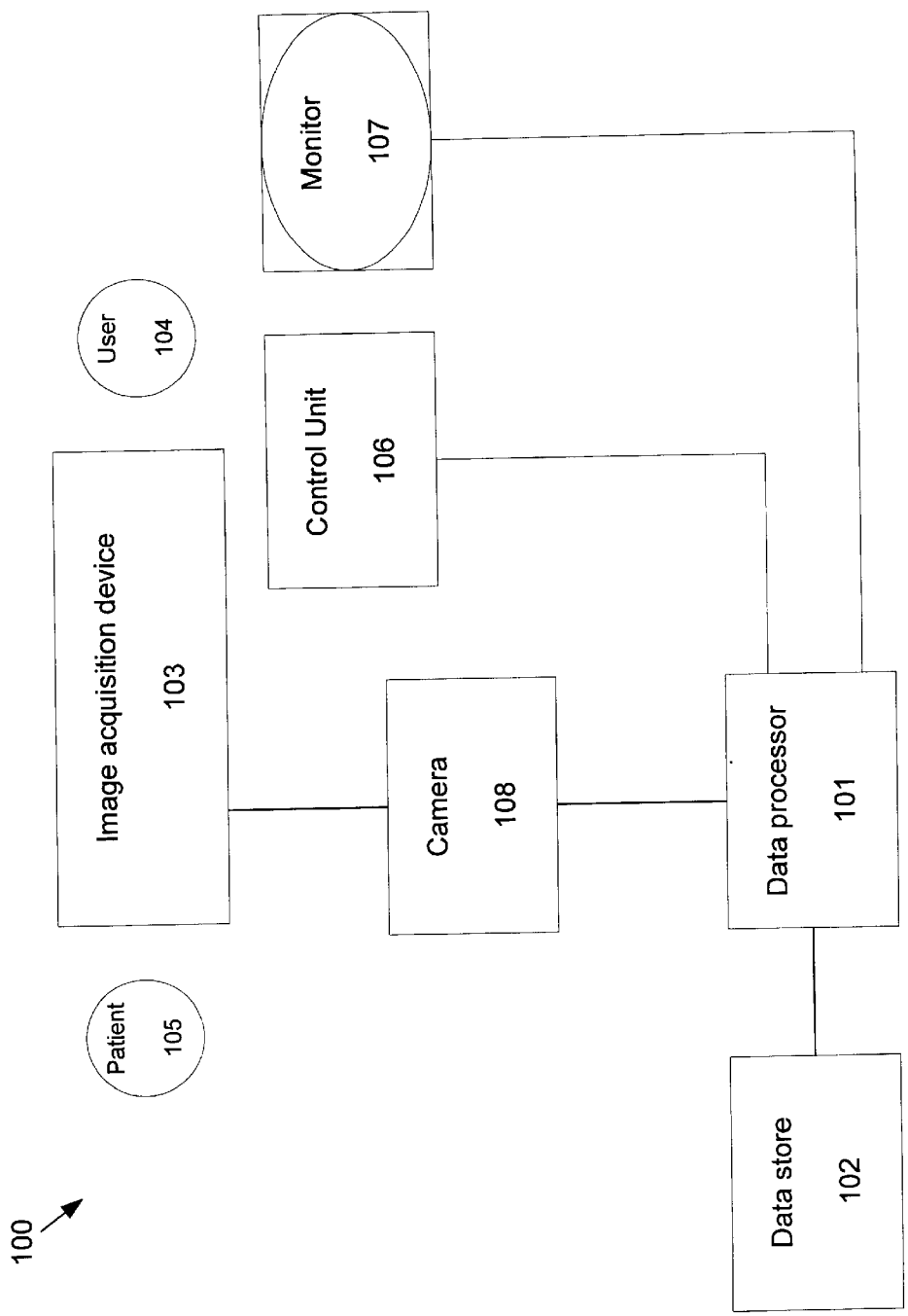
FIG. 1 is a block diagram of the image acquisition and mosaicing system, according to the invention.

FIG. 1 is a block diagram of the image acquisition and mosaicing system 100, according to the invention. Image acquisition device 103 is coupled to a camera 108. Image acquisition device 103 may be a direct opthalmoscope or a slitlamp biomicroscope, for example. The direct opthalmoscope may be a device commercially available from Welch-Allyn, Inc. The slitlamp biomicroscope may be a device commercially available from Nikon, Inc., model number NS-1V. User 104 looks through image acquisition device 103 at patient's eye 105. Camera 108 receives the image output of image acquisition device 103 and is coupled to a data processor 101. Camera 108 may be a CCD camera device adapted to receive images from the direct opthalmoscope and the slitlamp biomicroscope. It should also be appreciated that image acquisition device 103 and camera 108 may be a single unit, for example model number NS-1V available from Nikon, Inc. Data processor 101 is coupled to a data store 102, a monitor 107 and a control unit 106. Data store 102, data processor 101, and monitor 107, and control unit 106 may be a commercially available personal computer, wherein control unit 106 is a keyboard, mouse, or microphone coupled to voice-recognition software, familiar to those skilled in the art.

Figure 2:
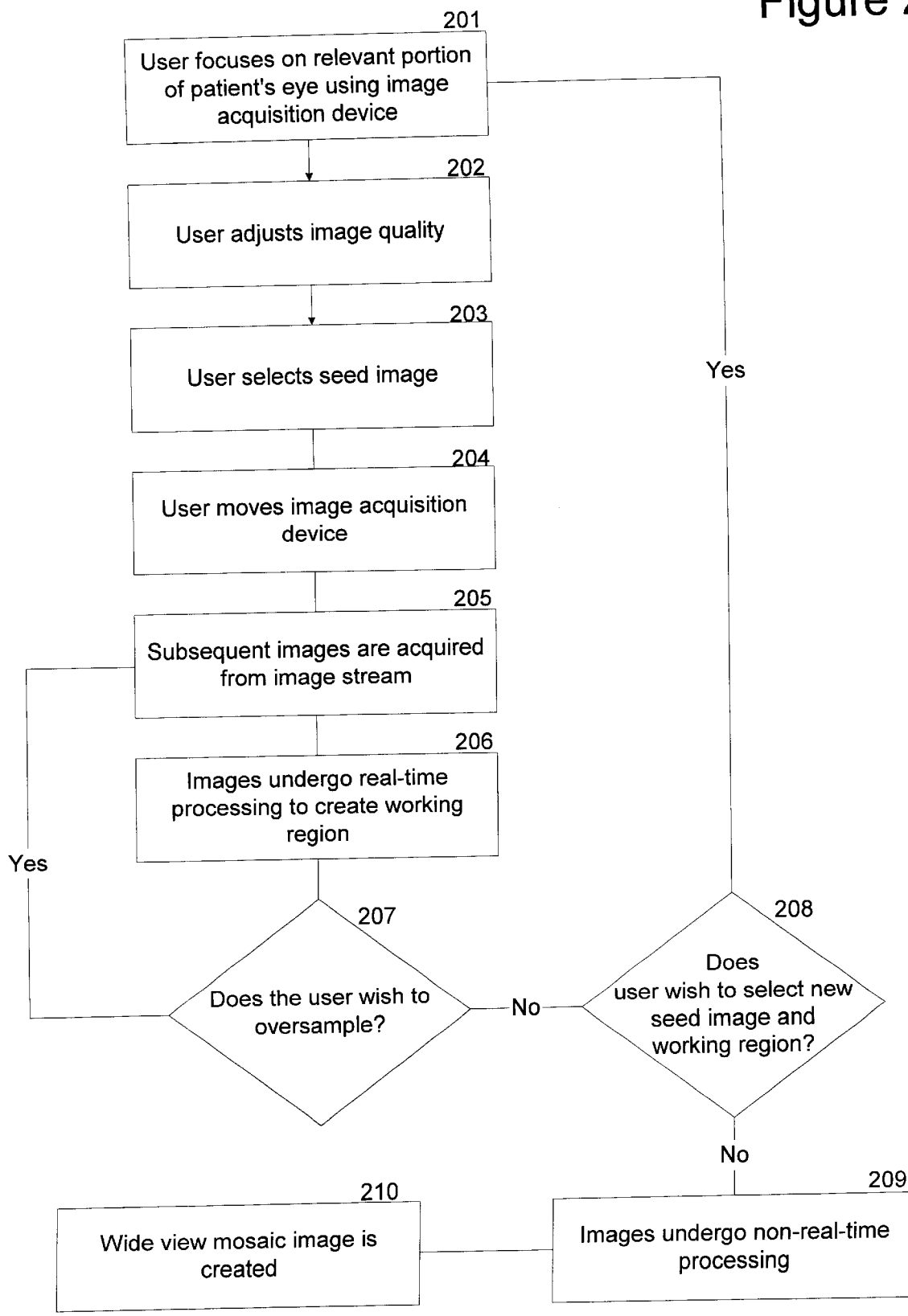
FIG. 2 illustrates the image acquisition and mosaicing system in real-time and non-real-time realms, according to the invention.

FIG. 2 is a flow chart detailing the operation of image acquisition and mosaicing system 100. In step 201, user 104 focuses on the relevant portion of patient's eye 105 using image acquisition device 103. User 104 is able to determine the relevant location by viewing the image that appears on monitor 107. More specifically, as user 104 looks through image acquisition device 103 and examines patient's eye 105, camera 108 receives the image from image acquisition device 103 and transmits it to data processor 101. In the case where camera 108 provides an analog-based image, or where camera 108 provides a digital image that is incompatible with data processor 101, the non-complying image may be converted to a proper digital image. Such conversion may be made by a separate converter (not shown) or by data processor 101. Data processor 101 then provides the image to monitor 107 where user 104 can view the image. User 104 may then move image acquisition device 103 so as to focus on the relevant portion of patient's eye 105. As user 104 moves image acquisition device 103, a continuous stream of images are processed by data processor 101 and appear on monitor 107. As a result, user 104 is provided with a view of patient's eye 105 that is continuously updated with the movement of image acquisition device 103.

In step 202, user 104 adjusts the quality of the image displayed on monitor 107 using control settings (not shown) on image acquisition device 103, for example, magnification and contrast settings. Once user 104 is satisfied with the quality of the image depicted on monitor 107, user 104 selects the image using control unit 106, in step 203. At this point, data processor 101 stores the depicted image in data store 102. The initial selected region is called the "seed" region. In step 204, user 104 moves image acquisition device 103 to view a different part of patient's eye 105. Images are continuously acquired by camera 100 and displayed on monitor 107 via data processor 101. In step 205, subsequent images to be added to the mosaic are gleaned automatically from the incoming image stream. As subsequent images are added, the "seed" image or the previously acquired image may be displayed and highlighted on monitor 107 so that user 104 may provide the necessary overlap among the images.

In step 206, the acquired images undergo real-time processing (i.e., align and merge overlapping acquired images) to create a "working" region of the multiple images. Real-time image processing is discussed in greater detail with reference to FIG. 3. Data processor 101 continues to perform real-time image processing each time subsequent images are added, thus expanding the working region. Once user 104 is satisfied that the working region is of sufficient scope, user 104 decides whether "oversampling" is necessary. Oversampling describes the process of acquiring multiple images of the same area so as to improve signal-to-noise ratio and image quality. If user 104 wishes to oversample, the process returns to step 205 and subsequent images again are acquired from the image stream. If, on the other hand, user 104 does not wish to oversample, user 104 determines whether a new seed image and corresponding working region is to be acquired, in step 208. If user 104 wishes to select a new seed image, the process returns to step 201. If, on the other hand, user 104 does not wish to select a new seed image, the acquired images (and perhaps multiple working regions) undergo non-real-time processing, in step 209. Non-real-time image processing is discussed in greater detail with reference to FIG. 4. At the conclusion of the non-real-time processing, a wide view mosaic image is created, in step 210.

Figure 3:
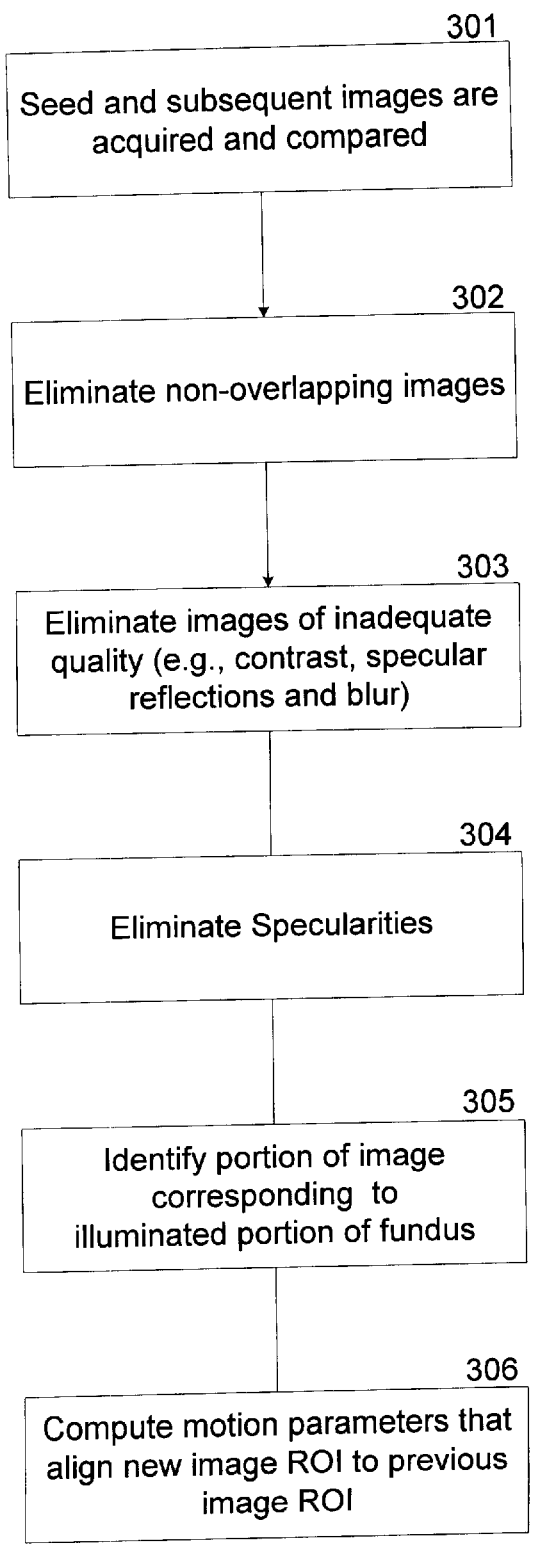
FIG. 3 is a flow chart detailing real-time processing of acquired images, according to the invention.
Figure 4:
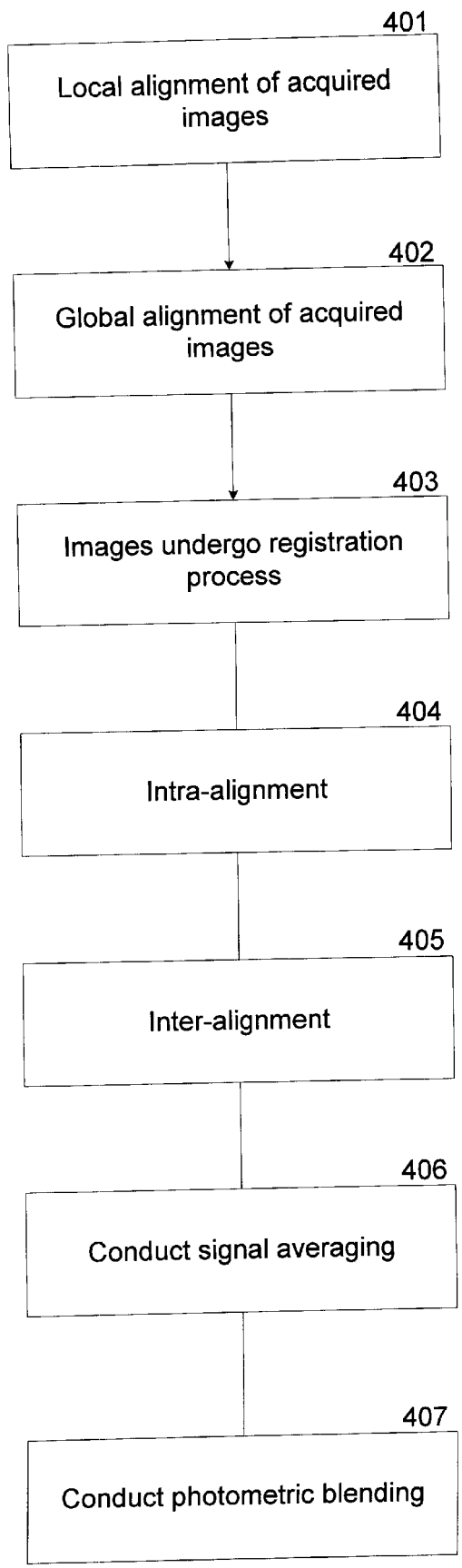
FIG. 4 is a flow chart detailing non-real-time processing of acquired images, according to the invention.

Data processor 101 may conduct a number of image processing techniques well known to those skilled in the art. Two such techniques include real-time and non-real-time processing, briefly described in steps 206 and 209, respectively, of FIG. 2. FIG. 3 is a flow chart detailing real-time processing and FIG. 4 is a flow chart detailing non-real-time processing. However, it should be appreciated that the invention is not limited to the techniques described in FIGS. 3 and 4.

FIG. 3 is a flow chart detailing real-time processing of acquired images. Generally, real-time image processing aligns and merges overlapping acquired images with the selected seed image, thus enlarging the seed image into a working region. As shown in FIG. 3, in step 301, seed and subsequent images are acquired and compared. Such comparison may take place in data processor 101. As user 104 attempts to visually ensure that there is some overlap between the working region and the next selected region, in step 302, real-time processing acts to merge only those acquired images that have such overlap and eliminate those images that do not. In step 303, real-time processing eliminates images with inadequate quality (e.g., contrast, specular reflections and blur), as judged by the magnitude of the similarity between the seed image and subsequent images. For each usable image, however, real-time processing excludes specularities in step 303, and computes a region of interest (ROI) (i.e., that portion of the image containing the fundus image without specular reflections) based on color, contrast, and texture, in step 304. In one embodiment, the ROI includes contiguous pixels located near the central portion of the image, and those pixels of intermediate brightness (i.e., greater than non-illuminated background but less than saturated pixels corresponding to specularities). The approximate fraction of the total image corresponding to the ROI may be specified by user 104, if need be.

In step 305, the portion of the image corresponding to the illuminated portion of the fundus image is identified. In step 306, real-time processing computes motion parameters (e.g., translation, rotation, and magnification) that align the ROI of the new image to the ROI of the previous image with a coarse-to-fine resolution registration process. This coarse-to-fine resolution registration process refines the estimate to minimize an objective function that measures the similarity between the previous and current image. In one embodiment, this process is extended to calculate motion estimates based not only on a comparison of the current image to the previous image, but on any set of previously acquired images in the sequence, thus allowing for the refinement of parameters based on predicted motion. Furthermore, real-time processing may conduct hierarchical motion estimates. Hierarchical motion estimates permit a scalable implementation where coarse alignments are always performed. In addition, increasingly finer alignments may be included as time permits. The current implementation constrains the overall displacement between successive images, and includes planar surface or affine flow. The result of the real-time registration process consists of a set of constituent images along with motion parameters for each working region. The motion parameters define the placement of each image with respect to its reference. In most instances, the reference will be the previous image.

It should be appreciated that the real-time processing may be repeated as more images are acquired, thus expanding the working region. It should also be appreciated that other real-time processing techniques, not described with reference to FIG. 3, also may be conducted.

FIG. 4 is a flow chart detailing non-real-time processing. More accurate than real-time processing, non-real-time processing generally aligns the overlapping images that have been acquired in real-time. In step 401, the acquired images are aligned locally. In step 402, the acquired images are aligned globally. In step 403, the locally and globally aligned images undergo a highly accurate image registration process. Specifically, highly accurate, sub-pixel resolution, image registration between frames may be conducted. This process allows for improved spatial resolution. Alignment of the working set of images into a wide field of view mosaic representation is accomplished in non-real-time by co-registration of each image with respect to the working region as a whole. Therefore, this image registration permits an expansion of the once narrow field of view into a high-quality, improved resolution, wide field of view ophthalmic image, suitable for diagnosis and treatment.

In one embodiment, optical flow is computed between the new image and the working region to recover a non-global displacement field. Multiple frames are averaged at original pixel locations and new pixels are created with increased resolution by a factor of two or more via interpolation. Averaging is conducted amongst those frames that contribute intensity at inter-pixel locations, as judged by sub-pixel accuracy registration. In one embodiment, the effective spatial sampling rate in each dimension may be increased by as much as a factor of two.

In step 404, a single working region is aligned, called "intra-alignment." The topological layout of the frames is inferred from the collection of individual parameter sets associated with each image. Frame sets (usually pairs) which are not adjacent in time, but do appear to have a large amount of overlap are registered. If the registration is successful as judged by the magnitude of a similarity, the resultant alignment information (i.e., parameters and associated image information) is added to the collection. This process is continued until the images that cover the mosaic region are sufficiently connected. The parameters comprising the mosaic "covering" are then refined to optimize the global alignment of the image set as a whole.

In step 405, multiple independent working regions are combined, called "inter-alignment." Multiple independent working regions may be merged prior to mosaicing by extension of this technique as long as the mapping relationship of one region is known with respect to the other. This relationship may consist of a single common overlapping image between the two or it may be based on user interaction and placement of one working region with respect to the other.

In step 406, non-real-time processing may also include signal averaging of the acquired images. This process increases the signal-to-noise ratio and overall resolution of the mosaic. Finally, in step 407, non-real-time processing may include various types of blending. Photometric blending corrects slight brightness variability that is expected when retinal features are imaged under varying optical conditions. In addition, computer 101 may conduct multi-resolution blending to smooth transitions in color and brightness between adjacent images. The blending boundary between adjacent images is drawn which selects the best quality section from each overlapping image. The overlapping images are decomposed into a multi-resolution representation (pyramid) and the images are then merged at each resolution level. The blending boundary is smoothed with a low-pass filter at each level and the full-resolution combined image is then reconstructed from the combined pyramid representation.

Resulting mosaics may be projected onto a planar or other surface. As both the outer and inner surfaces of the eye are approximately spherical, the current preferred embodiment is projection of the mosaic onto a spherical surface corresponding to an average eye size. Alternatively, ultrasound information, containing the true size of the examined eye, may be entered into processor 101 so as to allow the mosaic to be projected onto a spherical surface equal to the patient's specific eye dimensions.

Although several embodiments of the invention have been described in detail above, those skilled in the art will appreciate that numerous other modifications to the invention are possible within the scope of the invention. Accordingly, the scope of the invention is not intended to be limited to the preferred embodiments described above, but only by the appended claims.

What is claimed is:

1. A method of mosaicing images of the eye, comprising the steps of:
   acquiring a first image of the eye from a narrow field of view image acquisition device;
   acquiring a second image of the eye from said image acquisition device, wherein said second image includes a portion of said first image; and
   processing said images to produce a mosaic representation.

2. The method of claim 1, further comprising the step of providing a direct ophthalmoscope to conduct said steps of acquiring.

3. The method of claim 1, further comprising the step of providing a slitlamp biomicroscope to conduct said steps of acquiring.

4. The method of claim 1, wherein said processing step comprises the step of converting said images to a digital format.

5. The method of claim 1, further comprising the step of viewing said first image as a guide during the step of acquiring said second image.

6. The method of claim 1, wherein said processing step comprises the steps of aligning and merging said first and second images.

7. The method of claim 1, wherein said processing step comprises real-time processing and non-real-time processing steps.

8. The method of claim 7, wherein said real-time processing step includes at least one of the following steps: eliminating non-overlapping images, image registration, topology inference, local-to-global alignment, image fusion, signal estimation, and multiresolution blending.

9. The method of claim 7, wherein said non-real-time processing step includes at least one of the following steps: local alignment, global alignment, image registration, intra-alignment, inter-alignment, signal averaging, and photometric blending.

10. The method of claim 1, wherein said acquiring steps comprise receiving said images from said image acquisition device to a processor.

11. The method of claim 1, further comprising the step of receiving a selection of the first image prior to acquiring the first image.

12. The method of claim 11, further comprising the step of automatically acquiring subsequent images from said image acquisition device after receiving the selection of the first image.

13. The method of claim 12, further comprising the step of creating a working region from said acquired images.

14. The method of claim 13, further comprising the step of oversampling said working region to enhance the quality of said working region.

15. A system for mosaicing images of the eye, comprising:
    a narrow field of view image acquisition device adapted to provide first and second adjustment images of the eye;
    a camera coupled to said image acquisition device to capture said images;
    a data processor coupled to said camera to process said images into a mosaic representation; and
    a monitor coupled to said data processor to guide a user in acquiring images using said image acquisition device.

16. The system of claim 15, further comprising a data storage device coupled to said data processor for storing said images.

17. The system of claim 16, wherein said selection unit includes at least one of the following: a keyboard, a mouse, and a microphone.

18. The system of claim 15, further comprising a selection unit coupled to said data processor.

19. The system of claim 15, further comprising an analog-to-digital converter coupled to said image acquisition device and said data storage device.

20. The system of claim 15, wherein said image acquisition device is a direct opthalmoscope.

21. The system of claim 15, wherein said image acquisition device is a slitlamp biomicroscope.

22. The system of claim 15, wherein said processor processes said images in real-time using software adapted to do at least one of the following steps: eliminate non-overlapping images, provide image registration, provide topology inference, provide local-to-global alignment, provide image fusion, provide signal estimation, and provide multiresolution blending.

23. The system of claim 15, wherein said processor processes said images in non-real-time using software adapted to do at least one of the following: provide local alignment, provide global alignment, provide image registration, provide intra-alignment, provide inter-alignment, provide signal averaging, and provide photometric blending.

24. A method of detecting eye diseases, comprising the steps of:
    examining the eye using a narrow field of view image acquisition device;
    capturing images of the eye, wherein each of said images includes a portion of another image;

aligning and merging said images to create a mosaic representation;

viewing said mosaic representation; and detecting eye disease from said mosaic representation.

25. The method of claim 24, wherein said step of examining is conducted using a direct ophthalmoscope.

26. The method of claim 24, wherein said step of examining is conducted using a slitlamp biomicroscope.

27. The method of claim 24 wherein said steps of capturing images, and aligning and merging said images occur during said step of examining the eye.

28. The method of claim 24 wherein said step of capturing images comprises receiving said images from said image acquisition device to a processor.

29. A method of creating a mosaic representation of the eye, comprising the steps of:

providing a narrow field of view image acquisition device adapted to acquire images of the eye;

acquiring a first image of a first portion of the eye;

moving said image acquisition device to a second portion of the eye, wherein said second portion overlaps said first portion;

acquiring a second image of said second portion of the eye; and processing said images to create a mosaic representation of the eye.

30. The method of claim 29, wherein said steps of acquiring comprise the step of automatically capturing images from a stream of images.

31. The method of claim 29, wherein said step of providing an image acquisition device comprises the step of providing a direct ophthalmoscope.

32. The method of claim 29, wherein said step of providing an image acquisition device comprises the step of providing a slitlamp biomicroscope.

33. The method of claim 29, further comprising viewing said first image while conducting said step of moving.

34. The method of claim 29, wherein said step of processing comprises merging and aligning said first and second images.

35. A method for mosaicing direct ophthalmoscope images, comprising the steps of:

acquiring a first direct ophthalmoscope image;

converting said first image into a digital format;

acquiring at least one subsequent direct ophthalmoscope image, wherein said subsequent images reproduce a portion of a preceding image;

converting said images into a digital format;

processing said images during said steps of acquiring said images to guide acquisition of said subsequent images;

processing said images to increase resolution and quality of said images;

merging said images to produce a mosaic representation of said images; and processing said mosaic representation such that said mosaic representation provides a seamless representation of said images.

36. A method for mosaicing slitlamp images, comprising the steps of:

acquiring a first slitlamp image;

converting said first image into a digital format;

acquiring subsequent slitlamp images, wherein said subsequent images reproduce a portion of a preceding image;

converting said images into a digital format;

processing said images during said steps of acquiring said images to guide acquisition of additional images;

processing said images to increase resolution and quality of said images;

merging said images to produce: a mosaic representation of said images; and processing said mosaic representation such that said mosaic provides a seamless representation of said images.

* * * * *